United States Patent [19]
Galli

[11] Patent Number: 5,389,681
[45] Date of Patent: Feb. 14, 1995

[54] PARENTERAL SOLUTIONS FOR DICLOFENAC SALTS

[75] Inventor: Bruno Galli, Seltisberg, Switzerland

[73] Assignee: Ciba-Geigy Corporation, Ardsley, N.Y.

[21] Appl. No.: 129,885

[22] Filed: Sep. 30, 1993

[30] Foreign Application Priority Data

Oct. 22, 1992 [CH] Switzerland ............ 3275/92

[51] Int. Cl.⁶ .................................. A61K 31/195
[52] U.S. Cl. ................................................ 514/567
[58] Field of Search ...................................... 514/567

[56] References Cited

U.S. PATENT DOCUMENTS

| | | | |
|---|---|---|---|
| 4,309,421 | 1/1982 | Ghyczy et al. | 514/78 |
| 4,593,044 | 6/1986 | Metz | 514/557 |
| 4,711,906 | 12/1987 | von Stetten et al. | 514/561 |
| 5,079,001 | 1/1992 | Affolter | 514/567 |

OTHER PUBLICATIONS

A. F. Gunnison et al: Sulfite Hypersensitivity. A critical Review, CRC Critical Review in Toxicology, vol. 17 (1987), Issue 3, pp. 185–214.

Search Report, European Patent Application No. 93810720.8 Ciba–Geigy (1993).

Primary Examiner—Raymond J. Henley, III
Attorney, Agent, or Firm—Irving M. Fishman; Karen G. Kaiser

[57] ABSTRACT

The invention relates to a pharmaceutical composition in the form of a sterilizable parenteral solution comprising a diclofenac salt and stabilizers, such as ethyl lactate combined with glutathione or N-acetylcysteine.

4 Claims, No Drawings

PARENTERAL SOLUTIONS FOR DICLOFENAC SALTS

The invention relates to a pharmaceutical composition in the form of a sterilisable parenteral solution comprising a diclofenac salt and stabilisers, to a process for the preparation of that solution and to the use of stabilisers in that preparation process.

Various medicaments having different structures are available for the treatment of inflammatory diseases, for example rheumatism. Since such diseases are often chronic, treatment with anti-inflammatory medicaments (anti-inflammatory drugs, antiphlogistics) generally has to extend over a prolonged period, with a regular, uninterrupted supply of active ingredient. In particular, when administered perorally over long periods many non-steroidal anti-inflammatory drugs (NSAIDs) may cause side-effects throughout the gastro-intestinal tract, for example nausea, vomiting, epigastric pain and also gastric ulcers. In addition, the release of active ingredient from peroral dosage forms, such as tablets or dragées, is slow, which can be disadvantageous in the treatment of sudden acute rheumatic pain.

The preferred group of NSAIDs includes the sodium salt of diclofenac, which was introduced a considerable time ago in many countries and is obtainable in various dosage forms, such as dragées, suppositories or injection solutions, under the trade mark ®Voltarol (Ciba-Geigy).

It is known that small amounts of diclofenac salts in aqueous solution, especially at elevated temperature under heat-sterilisation conditions, can cyclise to form 1-(2,6-dichlorophenyl)-indolin-2-one with the splitting-off of hydroxide ions. Oxidation with oxygen present in the solution may result in the formation of further undesired secondary products.

In order to suppress oxidation reactions, antioxidants, inter alia from the group of reducing sulfur compounds, are added to injection solutions (see Pharmazeutische Technologie (Pharmaceutical Technology), published by Heinz Sucker et al., G. Thieme Verlag Stuttgart DE, 1978, page 313). For example, the commercially available injection solution comprising the active ingredient VOLTAROL (see Rote Liste (Red List) 1987, No. 05169, index of preformulated medicaments, Editio Cantor) comprises the excipient sodium disulfite (sodium pyrosulfite) which is permitted as an antioxidant for injectables. Reduction and/or decomposition reactions of those excipients can effect changes in the pH of the aqueous solution outside the physiologically acceptable range of from 7 to 8. After the addition of the antioxidant, the injection solution to be sterilised must therefore be neutralised or buffered in a subsequent step in order to meet the requirement that the pH conditions of a solution for parenteral, especially i.m., administration be physiologically acceptable.

Antioxidants from the group of reducing sulfur compounds are known to have allergenic potential with the risk of asthma attacks and anaphylactic shock; see the review article: Sulfite Hypersensitivity by A. F. Gunnison and D. W. Jacobsen in CRC Critical Reviews in Toxicology, Vol. 17 (1987), Issue 3, pages 185–214, see especially Section C, pages 195–197. The addition of sulfites to preformulated medicaments must therefore be declared and the packaging must carry a warning (Proposal U.S. Fed. Reg. 19.11.1985).

The problem underlying the present invention is to prepare a novel, improved, sulfite-free dosage form for the parenteral administration of diclofenac salts that has the advantage over heat-sterilisable injection solutions known hitherto both of a stable pH value and of improved tolerability of the antioxidant used, combined with rapid onset of activity and long-lasting action of the active ingredient at a therapeutic level.

That problem is solved by the present invention, which relates to a pharmaceutical composition in the form of a parenterally administrable injection solution comprising the active ingredient diclofenac or a pharmaceutically acceptable salt thereof. That injection solution comprises:

a) a pharmaceutically acceptable salt of diclofenac;

b) 1,2-propylene glycol or polyethylene glycol 300–400 as solubiliser;

c) a pharmaceutically acceptable stabiliser selected from the group consisting of glutathione, glutathione combined with a $C_{2-3}$alkanecarboxylic acid $C_{2-4}$alkyl ester, or with hydroxy-$C_{2-4}$alkanecarboxylic acid $C_{2-4}$alkyl ester or with N-acetylcysteine and N-acetylcysteine combined with a $C_{2-3}$alkanecarboxylic acid $C_{2-4}$alkyl ester or with hydroxy-$C_{2-4}$alkanecarboxylic acid $C_{2-4}$alkyl ester and d) a carrier liquid acceptable for injection formulations and, where appropriate, further excipients that are acceptable therefor.

When the stabilisers of component c) are used, no formation of oxidation products of the indolin-2-one compound beyond the permitted limits is detected. Likewise, the undesired formation of oxidation products of the diclofenac salt is effectively suppressed. In addition, the pH value of the solution remains constantly neutral over a long period of up to several months.

Within the context of the description of the invention, the terms and definitions mentioned hereinbefore and hereinafter have preferably the following meanings:

The term pharmaceutical composition defines a solution that is suitable for parenteral administration, especially i.m., but also i.v., and that can be used in the treatment of inflammatory conditions accompanied by pain, especially rheumatism.

Component a) - A pharmaceutically acceptable salt of diclofenac, o-(2,6-dichlorophenylamino)-phenylacetic acid, is especially an alkali metal salt, for example the sodium or the potassium salt, or the salt formed with an amine, for example a mono-, di- or tri- $C_1$–$C_4$alkylamine, for example diethyl- or triethyl-amine, hydroxy-$C_2$–$C_4$alkylamine, for example ethanolamine, or hydroxy-$C_2$–$C_4$alkyl-$C_1$–$C_4$alkylamine, for example dimethylethanolamine, or a quaternary ammonium salt, for example the tetramethylammonium salt or the choline salt of diclofenac.

Special preference is given to the sodium salt and the potassium salt of diclofenac, see Merck Index, Eleventh Edition No. 3071. Those salts are present in the injection solution in a dose of from approximately 25 mg to approximately 150 mg. The preferred active ingredient concentration in the pharmaceutical composition is from approximately 10 mg/ml to approximately 50 mg/ml.

Component b) - The solubiliser is 1,2-propylene glycol (1,2-propanediol, Merck Index Eleventh Edition No. 7868) or polyethylene glycol having a molecular weight of approximately 300–400 (Merck Index Eleventh Edition No. 7545). Those solubilisers are present in the pharmaceutical composition in an amount of from approximately 5 % to approximately 50 % (weight-/volume), preferably from approximately 20 % to approximately 35 %. The preferred amounts of that component per formulation are from 500 to 2000 mg, especially from 500 to 1000 mg.

Component c) - The pharmaceutically acceptable stabiliser $C_{2-3}$alkanecarboxylic acid $C_{2-4}$alkyl ester is, for example, ethyl acetate or ethyl propionate. A hydroxy-$C_{2-4}$alkanecarboxylic acid $C_{2-4}$alkyl ester is especially ethyl lactate. Racemic mixtures or optically pure forms (enantiomers) of lactic acid may be used as stabilisers. In a preferred embodiment, ethyl lactate in combination with glutathione or with N-acetylcysteine is used as stabiliser for the injectable pharmaceutical composition. It was also not known hitherto that under neutral or approximately neutral conditions that combination of excipients effectively stabilises the pH value of aqueous solutions comprising diclofenac salts.

Glutathione (see Merck Index Eleventh Edition No. 4369) is known as a pharmaceutical excipient; see R. Voigt, Lehrbuch der Pharmazeutischen Chemie (Textbook of Pharmaceutical Chemistry), 6th edition, Verlag Chemie Weinheim, Federal Republic of Germany, pages 504–506, in which the use of that excipient as an antioxidant for hydrophilic systems is described.

N-Acetyl-L-cysteine (see Merck Index Eleventh Edition No. 82) is known as a pharmaceutical excipient. Glutathione or N-acetylcysteine is present in a preferred amount of approximately from 1.0 to 5.0 mg per formulation. Combined with those stabilisers, ethyl lactate is added in a preferred amount of approximately from 0.02 to 3.0 mg.

The pharmaceutical composition comprises a total of from approximately 0.1 mg/ml to approximately 3 mg/ml, preferably from approximately 1 mg/ml to approximately 2 mg/ml, of component c).

The pharmaceutically acceptable carrier liquid d) is water that has been rendered germ- and pyrogen-free in accordance with the specifications of national pharmacopoeias for intravenous solutions.

The carrier liquid d) may comprise non-toxic excipients that are acceptable for injection formulations, for example water-soluble excipients required for establishing isotonic conditions, for example ionic additives, such as sodium chloride, or non-ionic additives, such as sorbitol, mannitol, glucose, lactose, fructose or sucrose. In particular, those additives, for example sodium chloride or mannitol, are present in the amounts prescribed in national pharmacopoeias that are required for establishing isotonic conditions in the injection solutions.

The volume of the carrier liquid d) in admixture with components a), b) and c) is, for example, approximately from 1 to 5 ml, preferably from 1 to 2 ml. In preferred forms, injection solutions comprising the customary doses of 50, 75 or 100 mg of diclofenac sodium have a total volume of approximately from 1 to 5 ml, preferably 3 ml.

The pharmaceutical composition according to the present invention can be used as an injection solution for parenteral administration, especially i.m. and i.v., in the treatment of pain, inflammation and/or rheumatic diseases in warm-blooded animals (humans). Daily doses of approximately from 25 to 200 mg of active ingredient can be administered, the individual dosage form comprising the customary amount of active ingredient of, for example, 25, 50, 75, 100 or 150 mg.

The invention relates also to a process for the preparation of the pharmaceutical composition. That process comprises dissolving components a), b) and c) in the carrier liquid d) in any desired order and, where appropriate, adding further excipients that are acceptable for injection formulations.

In a preferred form of the process, components a)—active ingredient—and b)—solubiliser—are added to the carrier liquid d). Component c)—stabilisers—is then added to that solution.

The active ingredient a) is added to a portion of the carrier liquid d) preferably in comminuted form, especially finely ground form. Finely ground diclofenac salt has a preferred average particle size of less than 200 μm and can be used especially at a particle size of less than 100 μm. To produce particles of that size, customary comminution techniques are used, for example grinding in an air-jet, ball or vibrator mill or by processes known per se in an ultrasound disintegrator, for example of the Branson Sonifier type, for example as described in J. Pharm. Sci. 53 (9), 1040–1045 (1965), or by means of high-speed stirring of a suspension, for example using a stirrer of the Homorex type from Brogli & Co., Basle.

The portion of carrier liquid d) to be used is approximately from 1 to 2 ml, to which are added all of the solubiliser b) as well as the finely ground active ingredient a) and the stabilisers c).

The slightly acidic aqueous solution is, for example, rendered basic to a pH of approximately 8.0. That can be effected by the addition of a pharmaceutically acceptable dilute aqueous base, for example dilute sodium hydroxide solution, preferably 0.1N NaOH solution. The addition is customarily carried out with simultaneous pH monitoring. If necessary the solution is made up to the required injection volume with sterile, germ-free and pyrogen-free water. The injection solution can be introduced under aseptic conditions into ampoules or injection vials of suitable capacity and heat-sterilised in an autoclave (above 120°/at least 15 min.).

The invention relates also to the use of the stabiliser c) selected from the group consisting of glutathione, glutathione combined with a $C_{2-3}$alkanecarboxylic acid $C_{2-4}$alkyl ester, or with hydroxy-$C_{2-4}$alkanecarboxylic acid $C_{2-4}$alkyl ester or with N-acetylcysteine and N-acetylcysteine combined with a $C_{2-3}$alkanecarboxylic acid $C_{2-4}$alkyl ester or with hydroxy-$C_{2-4}$alkanecarboxylic acid $C_{2-4}$alkyl ester in the process described hereinbefore.

The present invention relates preferably to a pharmaceutical composition in the form of a parenterally administrable injection solution comprising:

a) the sodium salt of diclofenac;

b) 1,2-propylene glycol or polyethylene glycol 300 as solubiliser;

c) ethyl lactate combined with glutathione or with N-acetylcysteine as stabilisers and d) a carrier liquid acceptable for injection formulations and, where appropriate, further excipients that are acceptable therefor.

The invention relates especially to the formulations described in the Examples.

The following Examples serve to illustrate the invention described in full above; they are not intended to limit the scope of that invention in any way.

EXAMPLE 1

| | |
|---|---|
| diclofenac sodium (®Voltarol) | 75.0 mg |
| 1,2-propylene glycol (dist.) | 1000.0 mg |
| ethyl lactate | 0.1 mg |
| glutathione or N-acetylcysteine | 2.0 mg |
| 1N NaOH solution | to pH 8.3 |
| water per injection | ad 3.0 ml |

A portion of the water is introduced under a nitrogen protecting gas atmosphere. All of the glutathione or N-acetylcysteine is dissolved therein. All of the 1,2-propylene glycol and the active ingredient, which has previously been ground to an average particle size of approximately 100 μm, are added thereto. The pH value of the solution is adjusted to pH 8.3 with 0.1N sodium hydroxide solution, and ethyl lactate is added. The solution is made up to 3 ml (per formulation) with water and then filtered using a sterile filter of 0.2 μm pore size (consisting, for example, of NYLON, polypropylene or acrylic copolymer) and then sterilised for 15 minutes at 121° C. 3.3 ml portions of the solution from the total batch are introduced into friable ampoules.

EXAMPLE 2

| | |
|---|---|
| diclofenac sodium (®Voltarol) | 75.0 mg |
| polyethylene glycol 300 | 1000.0 mg |
| glutathione or N-acetylcysteine | 2.0 mg |
| ethyl lactate | 0.1 mg |
| 1N NaOH solution | to pH 8.0 |
| water per injection | ad 3.0 ml |

A portion of the water is introduced under a nitrogen protecting gas atmosphere. All of the glutathione or N-acetylcysteine combined with ethyl lactate is dissolved therein. All of the polyethylene glycol 300 and the active ingredient, which has previously been ground to an average particle size of approximately 100 μm, are added thereto. The pH value of the solution is adjusted to pH 8.0 with 0.1N sodium hydroxide solution. The solution is made up to 3 ml (per formulation) with water and then filtered using a sterile filter of 0.2 μm pore size (consisting, for example, of NYLON, polypropylene or acrylic copolymer) and then sterilised for 15 minutes at 121° C. 3.3 ml portions of the solution from the total batch are introduced into friable ampoules.

EXAMPLE 3

(Analogous to Example 1 or 2)

| | |
|---|---|
| diclofenac sodium (®Voltarol) | 75.0 mg |
| polyethylene glycol 300 | 780 mg |
| benzyl alcohol | 120 mg |
| mannitol | 8.6 mg |
| ethyl lactate | 0.1 mg |
| glutathione or N-acetylcysteine | 2.0 mg |
| 1N NaOH solution | to pH 8.0 |
| water per injection | ad 2.0 ml or ad 3.0 ml |

EXAMPLE 4

(Analogous to Example 1 or 2)

| | |
|---|---|
| diclofenac sodium (®Voltarol) | 75.0 mg |
| 1,2-propylene glycol | 780 mg |
| benzyl alcohol | 120 mg |
| mannitol | 8.6 mg |
| ethyl lactate | 0.1 mg |
| glutathione or N-acetylcysteine | 2.0 mg |
| 1N NaOH solution | to pH 8.0 |
| water per injection | ad 2.0 ml or ad 3.0 ml |

What is claimed is:

1. A pharmaceutical composition in the form of a parenterally administrable solution consisting essentially of:
   a) a pharmaceutically acceptable salt of diclofenac;
   b) 1,2-propylene glycol or polyethylene glycol 300–400;
   c) glutathione admixed with $C_{2-3}$alkanecarboxylic acid $C_{2-4}$alkyl ester or with hydroxy-$C_{2-4}$alkanecarboxylic acid $C_{2-4}$alkyl ester; or N-acetylcysteine admixed with $C_{2-3}$alkanecarboxylic acid $C_{2-4}$alkyl ester or with hydroxy-$C_{2-4}$alkanecarboxylic acid $C_{2-4}$alkyl ester; and
   d) a carrier liquid acceptable for injectable formulations.

2. A pharmaceutical composition in the form of a parenterally administrable solution consisting essentially of:
   a) the sodium salt of diclofenac;
   b) 1,2-propylene glycol or polyethylene glycol 300;
   c) glutathione admixed with ethyl lactate; or N-acetylcysteine admixed with ethyl lactate; and
   d) a carrier liquid acceptable for injectable formulations.

3. A method for treating pain, inflammation or rheumatic diseases which consists of administering to a host in need of such treatment, a pharmaceutical composition according to claim 1 in the form of a parenterally administrable injection solution.

4. A method for treating pain, inflammation or rheumatic diseases which consists of administering to a host in need of such treatment, a pharmaceutical composition according to claim 2 in the form of a parenterally administrable injection solution.

* * * * *